(12) United States Patent
He et al.

(10) Patent No.: US 8,606,362 B2
(45) Date of Patent: Dec. 10, 2013

(54) CURRENT OUTPUT ARCHITECTURE FOR AN IMPLANTABLE STIMULATOR DEVICE

(75) Inventors: Yuping He, Northridge, CA (US); David K. L. Peterson, Saugus, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 956 days.

(21) Appl. No.: 11/177,503

(22) Filed: Jul. 8, 2005

(65) Prior Publication Data

US 2007/0038250 A1 Feb. 15, 2007

(51) Int. Cl.
*A61N 1/02* (2006.01)
(52) U.S. Cl.
USPC .......................................................... 607/46
(58) Field of Classification Search
USPC .................................. 607/46, 57, 64
See application file for complete search history.

(56) References Cited

U.S. PATENT DOCUMENTS

| | | | |
|---|---|---|---|
| 3,646,940 A | 3/1972 | Timm et al. | 128/421 |
| 3,724,467 A | 4/1973 | Avery et al. | 128/418 |
| 3,822,708 A | 7/1974 | Zilber | 128/419 R |
| 5,522,865 A | 6/1996 | Schulman et al. | |
| 5,603,726 A | 2/1997 | Schulman et al. | 607/57 |
| 5,649,970 A * | 7/1997 | Loeb et al. | 607/57 |
| 5,804,957 A * | 9/1998 | Coln | 607/72 |
| 6,161,042 A * | 12/2000 | Hartley et al. | 607/20 |
| 6,181,969 B1 | 1/2001 | Gord | |
| 6,301,505 B1 | 10/2001 | Money | 607/63 |
| 6,381,496 B1 | 4/2002 | Meadows et al. | 607/59 |
| 6,516,227 B1 | 2/2003 | Meadows et al. | |
| 6,690,974 B2 * | 2/2004 | Archer et al. | 607/45 |
| 7,180,760 B2 | 2/2007 | Varrichio et al. | |
| 7,532,936 B2 | 5/2009 | Erickson et al. | |

FOREIGN PATENT DOCUMENTS

| | | |
|---|---|---|
| WO | 00/76436 | 12/2000 |
| WO | 2005/101627 A1 | 10/2005 |

OTHER PUBLICATIONS

U.S. Appl. No. 11/138,632, filed May 26, 2005, Parramon et al.

* cited by examiner

*Primary Examiner* — Joseph Dietrich
(74) *Attorney, Agent, or Firm* — Wong, Cabello, Lutsch, Rutherford & Brucculeri, LLP.

(57) ABSTRACT

Disclosed herein are current output architectures for implantable stimulator devices. Current source and sink circuitry is divided into a plurality of stages, each of which is capable via an associated switch bank of sourcing or sinking an amount of current to or from any one of the electrodes of the device. The current source circuitry is distinct from the current sink circuitry, and the two share no common circuit nodes prior to connection to the electrodes. In other words, the current source circuitry and the current sink circuitry do not share a common node other than the electrodes. Each stage is preferably formed of a current mirror for receiving a reference current and outputting a scaled version of current to that stage's switch bank. The scalar at each stage can be set by wiring a desired number of output transistors in parallel. Preferably, the reference current to the current mirrors in the stages is controllable via a digital-to-analog converter (DAC), to globally control the overall magnitude of the current supply to the electrodes.

29 Claims, 11 Drawing Sheets

US 8,606,362 B2

CURRENT OUTPUT ARCHITECTURE FOR AN IMPLANTABLE STIMULATOR DEVICE

FIELD OF THE INVENTION

The present invention relates generally to implantable stimulator devices, e.g., a pulse generator used in a Spinal Cord Stimulation (SCS) system or other type of neural stimulation system. More particularly, the present invention relates to the output current source/sink architecture used to supply currents to/from the electrodes of the device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. A Spinal Cord Stimulation (SCS) system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF receiver is implanted. Alternatively, the electrode lead may directly connect with the IPG or RF receiver. For examples of other SCS systems and other stimulation system, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

An IPG may include one or more output current sources/sinks that are configured to supply/receive stimulating current to/from the electrodes on the IPG, and ultimately to/from tissue. For example, FIG. 1 shows an exemplary output current source 500 and a corresponding output current sink 501 used to stimulate tissue, exemplified generically as a load 505 (R). As one skilled in the art will understand, transistors M1 and M3 in the output current source 500, and transistors M2 and M4 in the output current sink, comprise a current mirror. However, other current source or sink circuitry can be used, such as that disclosed in U.S. patent application Ser. No. 11/138,632 ("the '632 application"), filed May 26, 2005, which is incorporated herein by reference in its entirety.

Both the source 500 and sink 501 are coupled to a current generator 506 configured to generate a reference current, $I_{ref}$. A suitable current generator is disclosed in U.S. Pat. No. 6,181,969 ("the '969 patent"), issued Jan. 30, 2001 in the name of inventor John C. Gord, which is incorporated herein by reference in its entirety. The reference current in both the output current source/sink 500/501 is input into a digital-to-analog converter (DAC) configured to regulate the current that is delivered to the load 505. Thus, source 500 employs DAC circuitry 502, while sink 501 employs DAC circuitry 503, which circuit is illustrated only generically here but is fully disclosed in the above-incorporated '969 patent.

DAC circuitry 502, 503 is configured to regulate and/or amplify $I_{ref}$ and to output an output current $I_{out}$. Specifically, the relation between $I_{out}$ and $I_{ref}$ is determined in accordance with input bits arriving on busses 513, 513', which gives DAC circuitry 502, 503 its digital-to-analog functionality. Essentially, in accordance with the values of the various M bits on bus 513, any number of output stages (i.e., transistors M1, M2) are tied together in parallel such that $I_{out}$ can range from $I_{ref}$ to $2^M * I_{ref}$. (Fractional values of $I_{ref}$ are also possible, as disclosed in the '969 patent, but such subtlety is ignored herein for simplicity). Although not shown in FIG. 1, the output stages can contain other structures, such as choke transistors and other transistors designed to ensure good current matching in the current mirror circuitry. However, as such other structures are explained in the above-incorporated '969 patent, they are not discussed further.

As shown in FIG. 1, the output current source 500 is coupled to an electrode $E_X$ on the IPG device 100, while the output current sink 501 is coupled to a different electrode $E_Y$ on the IPG device. As explained in the above-incorporated '969 patent, an electrode will typically be hard-wired to both an output current source 500 and an output current sink 501, only one (or neither) of which is activated at a particular time to allow the electrode to selectively be used as either a source or sink (or as neither). Thus, for example, in FIG. 2A, four exemplary electrodes $E_1$, $E_2$, $E_3$, and $E_4$ are shown, each having their own dedicated source 500 and sink 501.

The source 500 and sink 501 hard-wired at each electrode are sometimes respectively referred to as PDACs and NDACs, reflecting the fact that the sources 500 are typically formed of P-type transistors while the sinks 501 are typically formed of N-type transistors. The use of transistors of these polarities is sensible given that the source is biased to a high voltage (V+), where P-type transistors are most logical, while the sink is biased to a low voltage (V−), where N-type transistors are most logical, as shown in FIG. 1. The substrate connection (not shown) for the transistors would typically be tied to the appropriate power supply, either V+ or V−, but could also be tied to the transistors' sources.

As shown in FIG. 2A, output current source 500 may be associated with electrode E2 (e.g., $E_X$ of FIG. 1) on the IPG at a particular point in time, while output current sink 501 may be associated with electrode E3 (e.g., $E_Y$ of FIG. 1) at that time. At a later time, electrodes E2 and E3 could be switched such that E2 now operates as the sink, while E3 operates as the source, or new sources or sinks could be chosen, etc.

A consequence of this architecture is that, as mentioned, each electrode has its own dedicated source (i.e., PDAC) and sink (i.e., NDAC) circuitry, as shown in FIG. 2A. Consider an approach disclosed in the '969 patent, which is illustrated in FIG. 3. Shown is the dedicated output current source circuitry for a particular electrode (e.g., $E_X$). Dedicated output current sink circuitry, similar to the output current source circuitry 500 but differing in polarity, would likewise be hardwired to the electrode $E_X$, but is not shown for convenience. Also not shown for convenience is the presence of a coupling capacitor (see '969 patent, FIG. 3, element 203). As shown, the source is capable of outputting to the electrode a current $I_{out}$ ranging from $I_{ref}$ to $127 I_{ref}$ in increments of $I_{ref}$, depending on the status of the control bits (Bit<1:M>). Specifically, each bit, when selected, contributes $2^{(M-1)}$ worth of current to the output current, $I_{out}$, through activation of pass transistors 530 in each of the M stages that comprise the output current source. For example, if a current of $53 I_{ref}$ is desired at $I_{out}$, bits Bit<1, 3, 5, 6> would be enabled (active low) to turn on transistors 530₁, 530₃, 530₅, and 530₆, which respectively contribute $I_{ref}$, $4 I_{ref}$, $16 I_{ref}$ and $32 I_{ref}$, in sum, $53 I_{ref}$. Although each stage is shown as having its own current source $I_{ref}$, it would usually be the case that each stage taps into a singular reference current (not shown for convenience), which is preferred to ensure current uniformity across the stages.

However, this approach does not comprise an efficient use of space on the integrated circuit on which the output current source/sink circuitry is fabricated. In a typical SCS system implementation, the SCS device might contain 16 electrodes, $E_1$ through $E_{16}$. However, it is usually the case that only one PDAC (source) and one NDAC (sink) are active at one time. Or, more rarely, four or more PDACs (sources) or NDACs (sinks) might be active at one time. Even in the more extreme cases, it will be noted that the majority of the PDACs (source) and NDACs (sinks) are inactive. In other words, most of the time, most of the PDACs or NDACs dedicated to a particular electrode are not being utilized. When one considers that the PDACs or NDACs take up significant space on the integrated circuit (see FIG. 3), the provision of such redundancy for every electrode seems inefficient.

Another output current architecture is disclosed in the above-incorporated '227 patent, and in particular in FIG. 4A of the '227 patent, salient aspects of which are summarized in the present application in FIG. 2B. As shown in FIG. 2B, the architecture of the '227 patent also uses a plurality of current sources and sinks, and further uses a low impedance switching matrix that intervenes between the sources/sinks and the electrodes $E_X$. Notice that each source/sink pair is hard-wired together at nodes 333, such that the switching matrix intervenes between the common nodes 333 and the electrodes. Of course, only one of the source or the sink in each pair is activated at one time, and thus point 333 in any pair will source or sink current at any particular time. Through appropriate control of the switching matrix, any of the nodes 333 may be connected to any of the electrodes $E_X$ at any time.

While generally a suitable architecture, the architecture of FIG. 2B suffers from drawbacks. For one, the FIG. 2B architecture puts additional resistance in the output path between the power supply in the DAC circuitry and the electrode. As explained in the above-incorporated '632 application, it is generally desired to minimize resistance between the power supply and the electrode. Thus, and referring to FIG. 4, which shows the architecture of FIG. 2B in further detail, it is desired that the resistance be minimized in the output path between the power supply V+ or V– and a given electrode $E_X$. This is because any resistance in the output path will give rise to a voltage drop in the output path (the output path resistance times $I_{out}$) which is not otherwise useful in the context of the circuitry. But in the architecture of FIGS. 2B and 4, it can be seen that three elements are serially connected between the power supplies and the electrode: the current mirror, the bit select transistor, and the transistor in the low impedance switch matrix. Due to the additional resistances of these components, and the additional resistance of the switches in the switch matrix, power (i.e., the output path resistance times $I_{out}^2$) is wasted. In an implantable stimulator device, such unnecessary power loss is regrettable, because battery life in such devices is critical and beneficially made as long lasting as possible.

Moreover, the architecture of FIG. 2B is further inefficient from a layout perspective. Due to the common node between a given PDAC source and NDAC sink pair, only one DAC in each pair can be active at any time. Thus, and like the architecture of FIG. 2A, DAC circuitry is guaranteed to go unused at any particular time. More specifically, at least 50% of the DAC circuitry (possibly more) will go unused at any given time, which again is a wasteful use of layout on the integrated circuit.

In short, the implantable stimulator art, or more specifically the IPG or SCS system art, would be benefited by an architecture that allowed variable currents to be provided at a number of electrodes, but in a more efficient manner. Such solutions are provided herein.

SUMMARY

Disclosed herein is a current output architecture for an implantable stimulator device such as an Implantable Pulse Generator (IPG) or more specifically for a Spinal Cord Stimulation (SCS) system. In the architecture, current source and sink circuitry is divided into a plurality of stages, each of which is capable via an associated switch bank of sourcing or sinking an amount of current to or from any one of the electrodes on the device. In the architecture, the current source circuitry is distinct from the current sink circuitry, and the two share no common circuit nodes prior to connection to the electrodes. In other words, the current source circuitry and the current sink circuitry do not share a common node other than the electrodes.

Each stage is preferably formed of a current mirror for receiving a reference current and outputting a current to that stage's switch bank. The output current in the stage preferably represents a scaled version of the reference current, i.e., the output current comprises the reference current times a scalar at the stage. The scalar at each stage can be set by wiring a desired number of output transistors in parallel. In a preferred embodiment, the scalars of the different stages are set to ensure that a minimum resolution of current can be supplied to any given electrode at any given time, a goal that may be achieved by setting the scalars to one in each stage. However, it should be realized that the scalars of the various stages can be widely varied to achieve particular design goals.

In a preferred embodiment, the reference current to the current mirrors in the stages is controllable. Specifically, and in one implementation, an initial reference current is input into a digital-to-analog converter (DAC) to provide a gain to the initial reference current, which is then provided to the stages. In so doing, the overall magnitude of the current to the electrodes on the device can be globally controlled by controlling the DAC. Any suitable current DAC circuitry can be used to scale the initial reference current.

With this architecture, dedicated source and sink circuitry are not required at every electrode on the device, because the stages in the source and sink circuitry are distributed across the electrodes by the switch banks. This improves system efficiency, and removes the waste of dedicated PDAC and NDAC circuitry not being used at unstimulated electrodes. Moreover, because the source and sink circuitry do not share a common node prior to the electrodes, difficulties associated with a particular node in the current supply circuitry potentially acting as both a source and sink are alleviated.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from efficient output current source/sink circuitry. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc.

Figure 5:
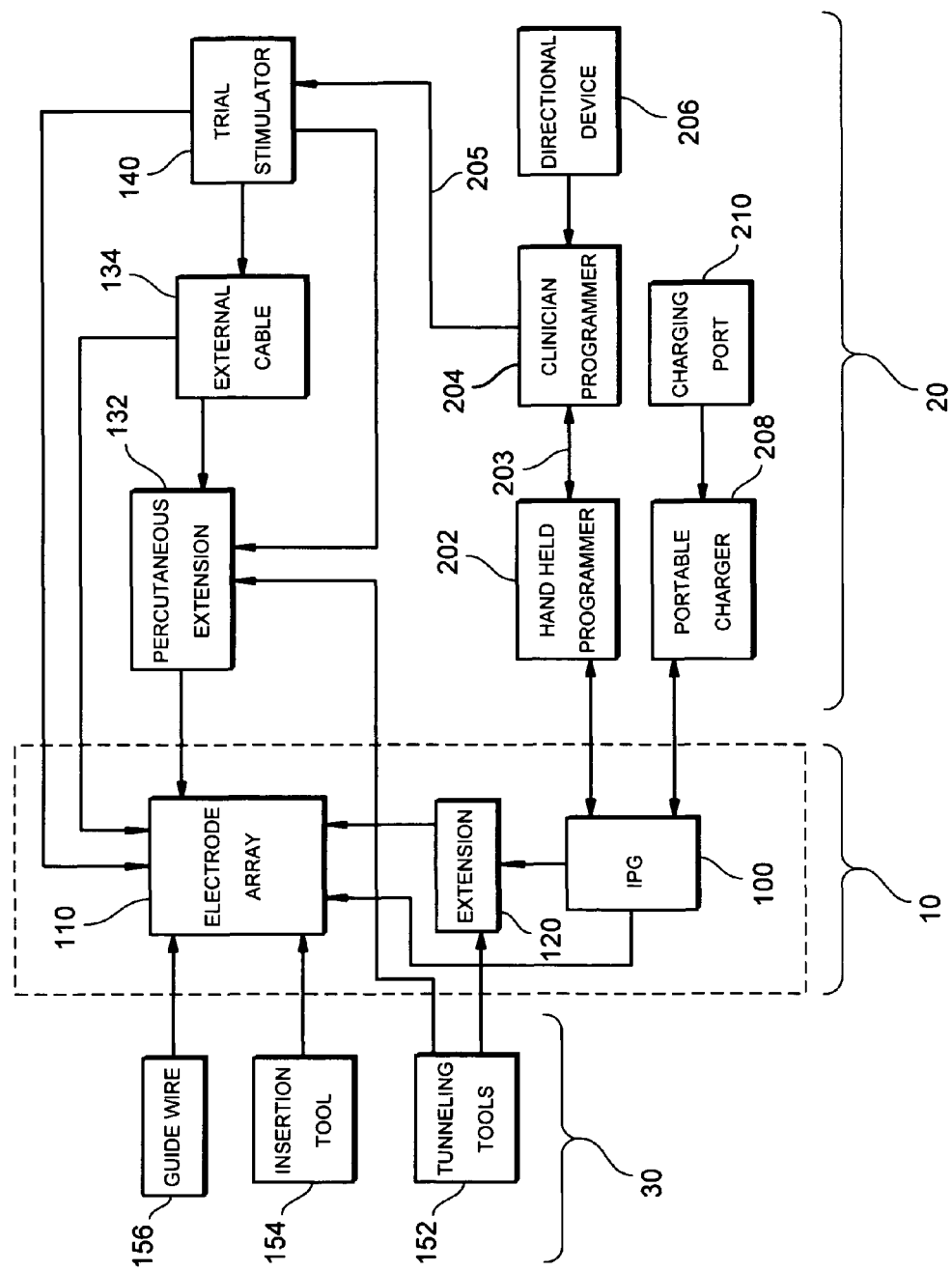
FIG. 5 shows a block diagram that illustrates exemplary implantable, external, and surgical components of a spinal cord stimulation (SCS) system that employs an implantable stimulator device in accordance with the present invention.

Turning first to FIG. 5, a block diagram is shown that illustrates the various components of an exemplary SCS system in which the invention may be used. These components may be subdivided into three broad categories: (1) implantable components 10, (2) external components 20, and (3) surgical components 30. As seen in FIG. 5, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below in connection with FIG. 7 or 8, may comprise a rechargeable, multichannel, telemetry-controlled, pulse generator housed in a rounded high-resistivity titanium alloy case to reduce eddy current heating during the inductive charging process. The IPG 100 may provide electrical stimulation through a multiplicity of electrodes, e.g., sixteen electrodes $E_1$ through $E_{16}$, included within the electrode array 110.

According to an exemplary embodiment of the present invention, the IPG 100 may include stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the IPG 100 may be replaced when its power source fails or is no longer rechargeable.

Figure 6:
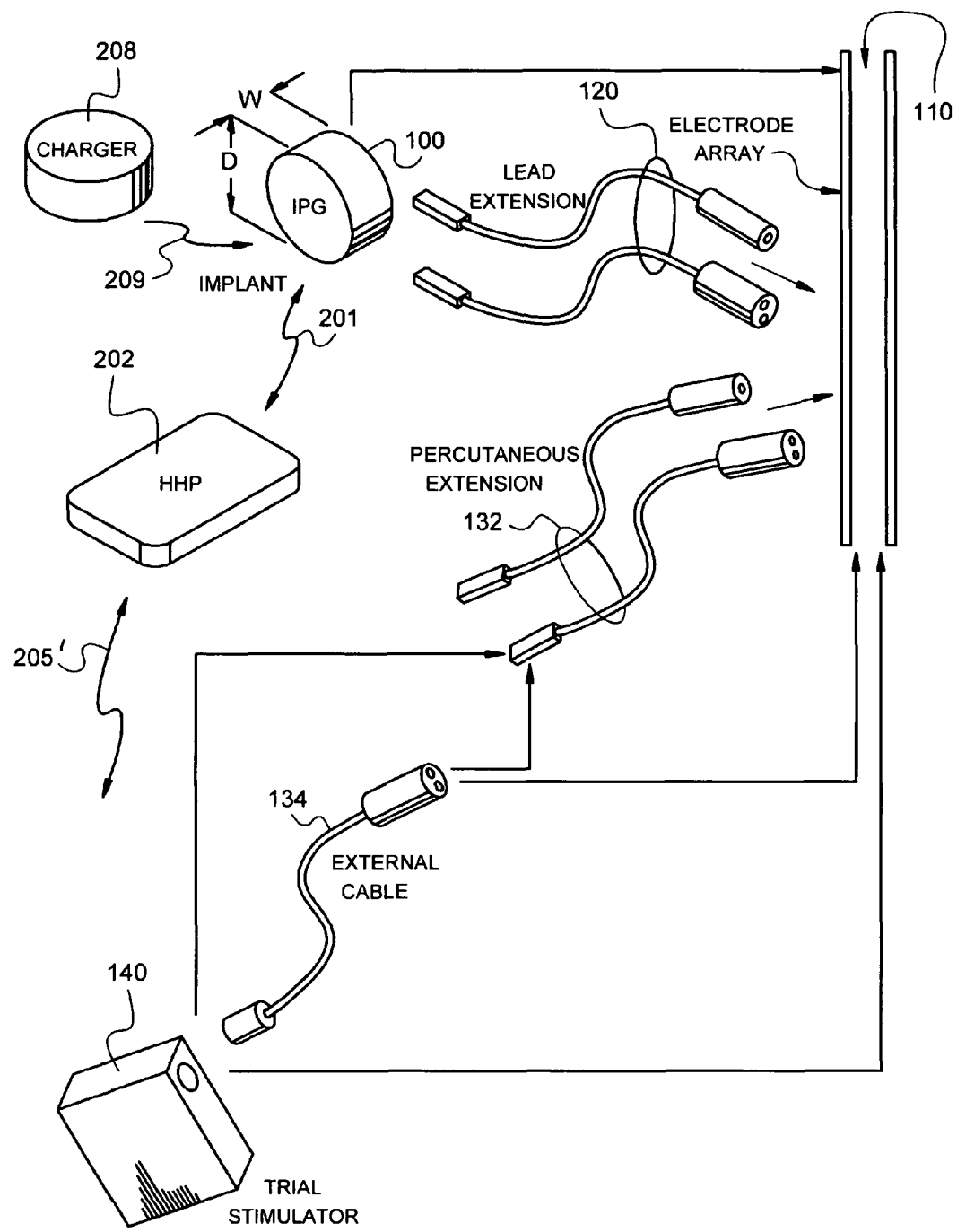
FIG. 6 shows various components of the SCS system of FIG. 5.

As seen best in FIG. 6, and as also illustrated in FIG. 5, the electrode array 110 and its associated lead system typically interface with the implantable pulse generator (IPG) 100 via a lead extension system 120. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis for, e.g., 7-10 days after the electrode array has been implanted, prior to implantation of the IPG 100, to test the effectiveness of the stimulation that is to be provided.

Still with reference to FIGS. 5 and 6, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set within prescribed limits. The HHP 202 may also be linked with the external trial stimulator 140 through another link 205', e.g., an infra red link. Detailed programming of the IPG 100 is preferably accomplished through the use of an external clinician's programmer 204 (FIG. 5), which may also be hand-held and which may be coupled to the IPG 100 directly or through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

Figure 7:
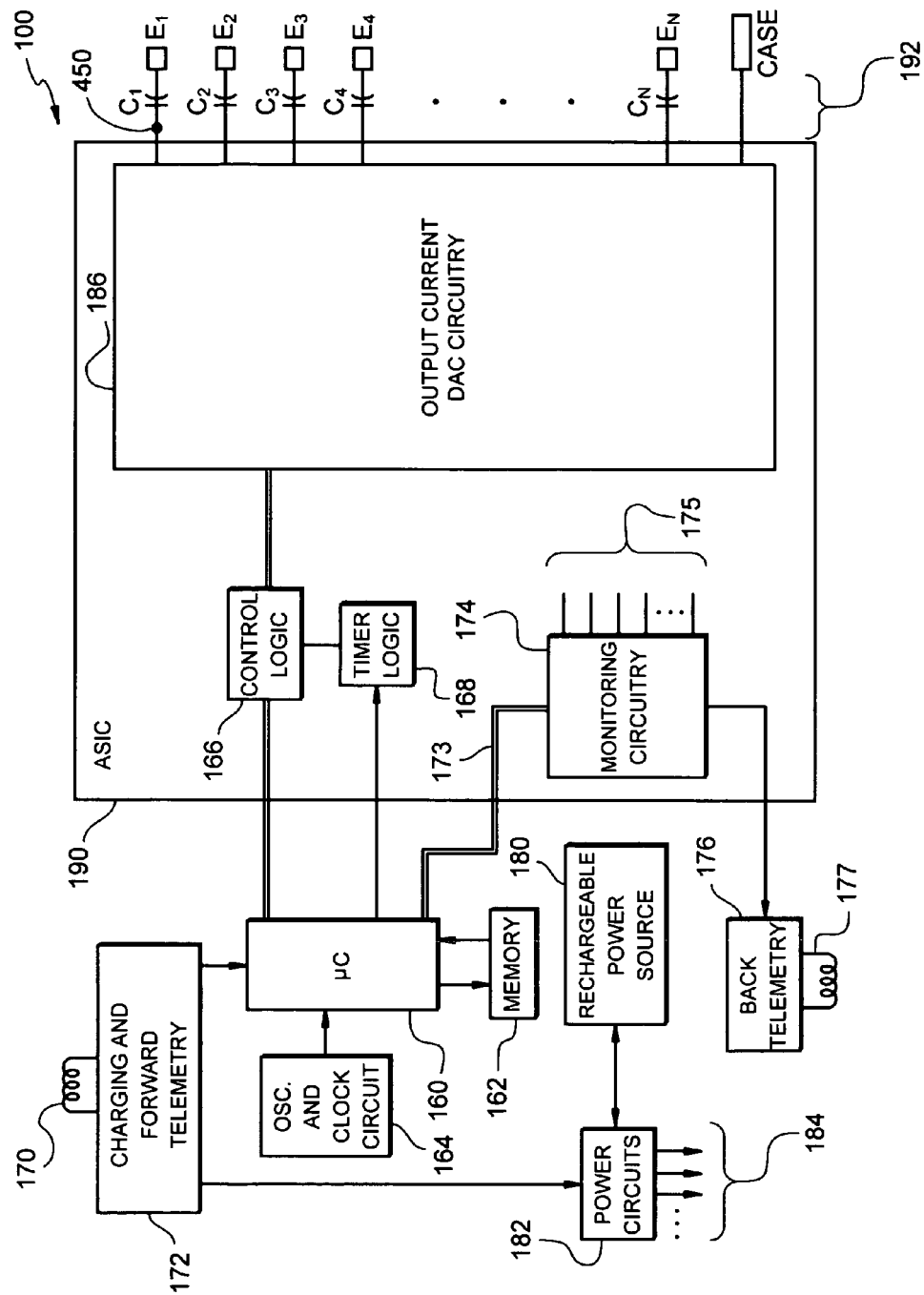
FIG. 7 shows a block diagram that illustrates the main components of one embodiment of an implantable stimulator device in which the invention can be used.

Turning next to FIG. 7, a block diagram is shown that illustrates the main components of one embodiment of an implantable pulse generator (IPG) 100 that may be used with the invention. As seen in FIG. 7, the IPG may include a microcontroller (μC) 160 connected to memory circuitry 162.

The μC 160 typically comprises a microprocessor and associated logic circuitry, which in combination with control logic circuits 166, timer logic 168, and an oscillator and clock circuit 164, generate the necessary control and status signals which allow the μC 160 to control the operation of the IPG in accordance with a selected operating program and stimulation parameters. The operating program and stimulation parameters are typically stored within the memory 162 by transmitting an appropriate modulated carrier signal through a receiving coil 170 and charging and forward telemetry circuitry 172 from an external programming unit, e.g., a handheld programmer 202 and/or a clinician programmer 204, assisted as required through the use of a directional device 206 (see FIG. 5). (The handheld programmer is thus considered to be in "telecommunicative" contact with the IPG; and the clinician programmer is likewise considered to be in telecommunicative contact with the IPG, e.g., through the handheld programmer). The charging and forward telemetry circuitry 172 demodulates the carrier signal it receives through the coil 170 to recover the programming data, e.g., the operating program and/or the stimulation parameters, which programming data is then stored within the memory 162, or within other memory elements (not shown) distributed throughout the IPG 100.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through back telemetry circuitry 176, which includes a transmission coil 177.

The operating power for the IPG 100 may be derived from a rechargeable power source 180 according to an exemplary embodiment of the present invention. The rechargeable power source 180 may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the patient hand held programmer 202. External programming software in the clinician programmer 204 is typically used to set parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode contact may be programmed to one of several discrete current levels, e.g., between 0 to 10 mA in steps of 0.1 mA. Also, the pulse width of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charged balanced. This means that the amount of positive charge associated with a given stimulus pulse are offset with an equal and opposite negative charge. Charge balance may be achieved through coupling capacitors $C_X$, which provide a passive capacitor discharge that achieves the desired charge balanced condition. Alternatively, active biphasic or multiphasic pulses with positive and negative phases that are balanced may be used to achieve the needed charge balanced condition.

In short, the IPG 100 is able to individually control the currents at the N electrodes. Controlling the output current DAC circuitry 186 using the microcontroller 160, in combination with the control logic 166 and timer logic 168, thereby allows each electrode contact to be paired or grouped with other electrode contacts, including the monopolar case electrode, to control the polarity, amplitude, rate, pulse width and channel through which the current stimulus pulses are provided.

As shown in FIG. 7, much of circuitry included within the IPG 100 may be realized on a single application specific integrated circuit (ASIC) 190. This allows the overall size of the IPG 100 to be quite small, and readily housed within a suitable hermetically-sealed case. The IPG 100 may include N feedthroughs to allow electrical contact to be individually made from inside of the hermetically-sealed case with the N electrodes that form part of the lead system outside of the case.

As noted earlier, in use, the IPG 100 may be placed in a surgically-made pocket, e.g., in the abdomen or just at the top of the buttocks, and detachably connected to the lead system (comprising optional lead extension 120 and electrode array 110). While the lead system is intended to be permanent, the IPG 100 may be replaced should its power source fail, or for other reasons.

The back telemetry features of the IPG 100 allow the status of the IPG to be checked. For example, when the external hand-held programmer 202 (and/or the clinician programmer 204), initiates a programming session with the IPG 100 (FIG. 5), the capacity of the battery is telemetered so that the external programmer can calculate the estimated time to recharge. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Figure 8:
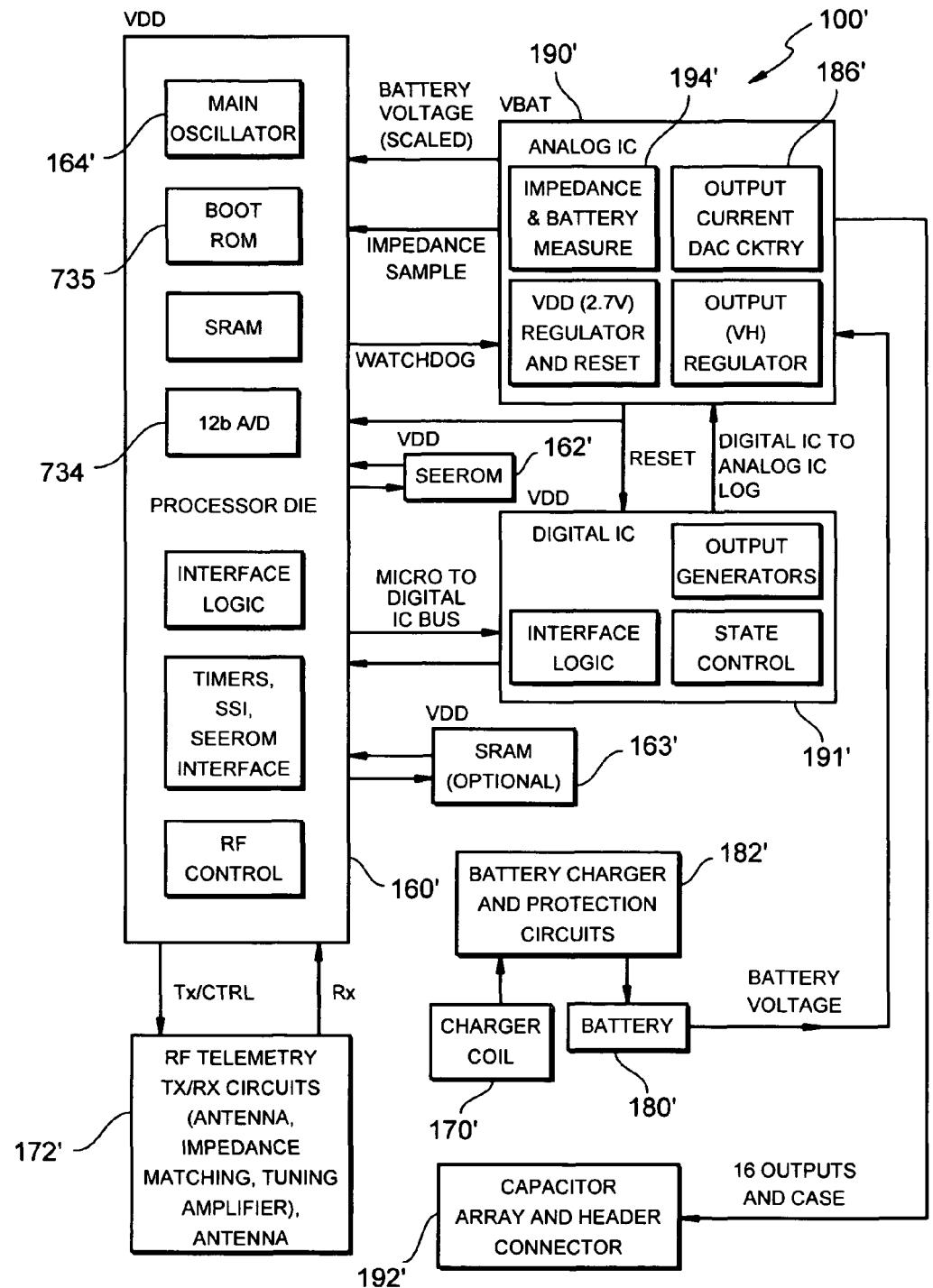
FIG. 8 shows a block diagram that illustrates another embodiment of an implantable stimulator device in which the invention can be used.

Turning next to FIG. 8, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 7. The IPG 100' includes a processor die, or chip, 160', an RF telemetry circuit 172' (typically realized with discrete components), a charger coil 170', a lithium ion or lithium ion polymer battery 180', battery charger and protection circuits 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, 16 kilobytes of SRAM memory, two synchronous serial interface circuits, a serial EEPROM interface, and a ROM boot loader 735. The processor die 160' may further include an efficient clock oscillator circuit 164' and a mixer and modulator/demodulator circuit implementing the QFAST RF telemetry method supporting bi-directional telemetry at 8 Kbits/second. QFAST stands for "Quadrature Fast Acquisition Spread Spectrum Technique," and represents a known and viable approach for modulating and demodulating data. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment. The output current DAC circuitry 186' will be described in more detail below with reference to FIGS. 9-11.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_X$ and electrodes $E_X$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1$, $E_2$, $E_3$, . . . , or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

As noted earlier, exemplary embodiments of the present invention involve the architecture used in the output current sources and sinks, i.e., in the output current DAC circuitry 186 or 186', which are sometimes respectively referred to as the PDAC and NDAC circuitry. Previous approaches were summarized in the Background section of this disclosure, and were illustrated primarily with respect to FIGS. 2 through 4. But as noted, these architectures suffered from various drawbacks.

Figure 9:
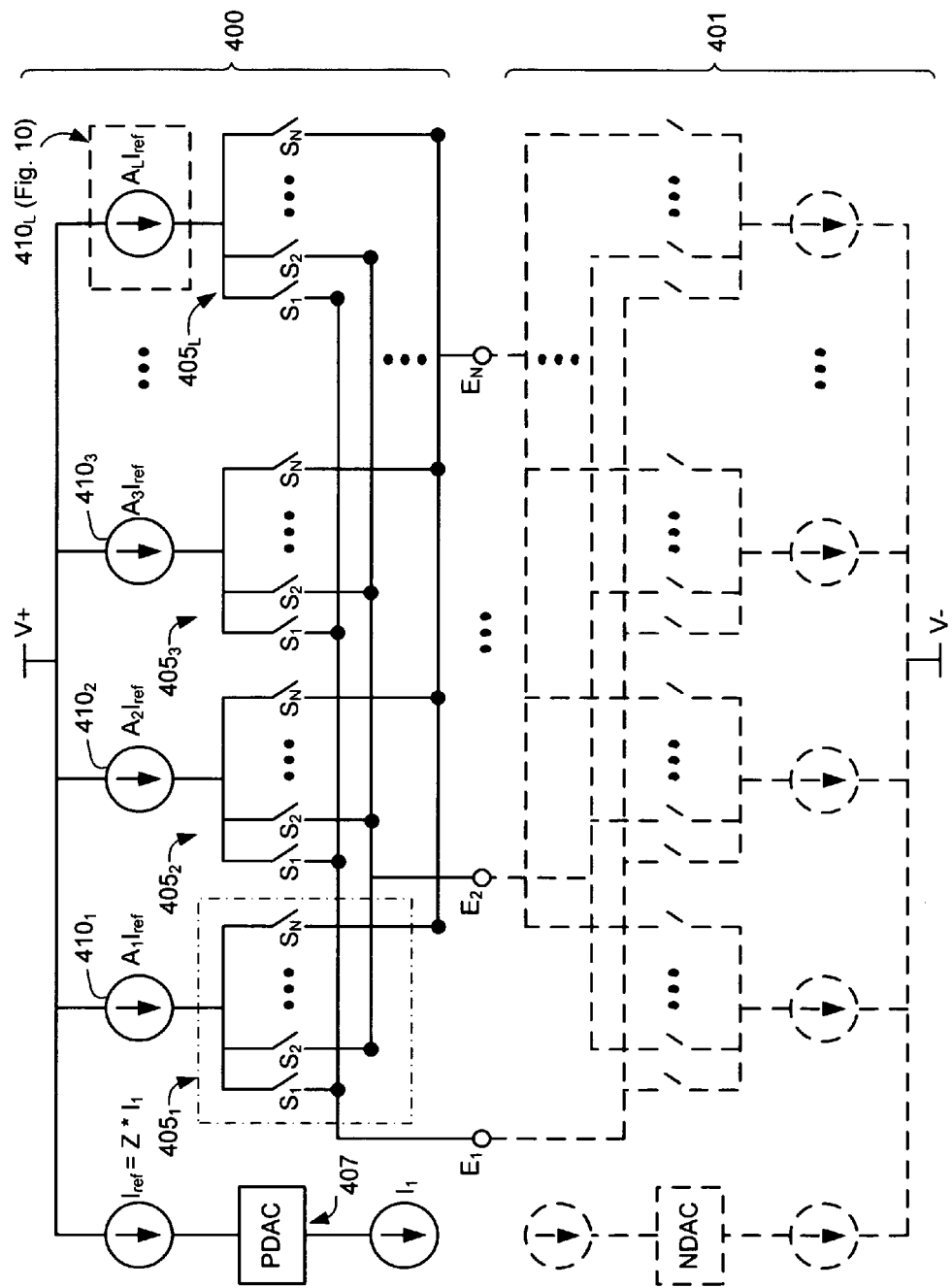
FIG. 9 illustrates an improved current source/sink architecture in accordance with one embodiment of the invention.
Figure 10:
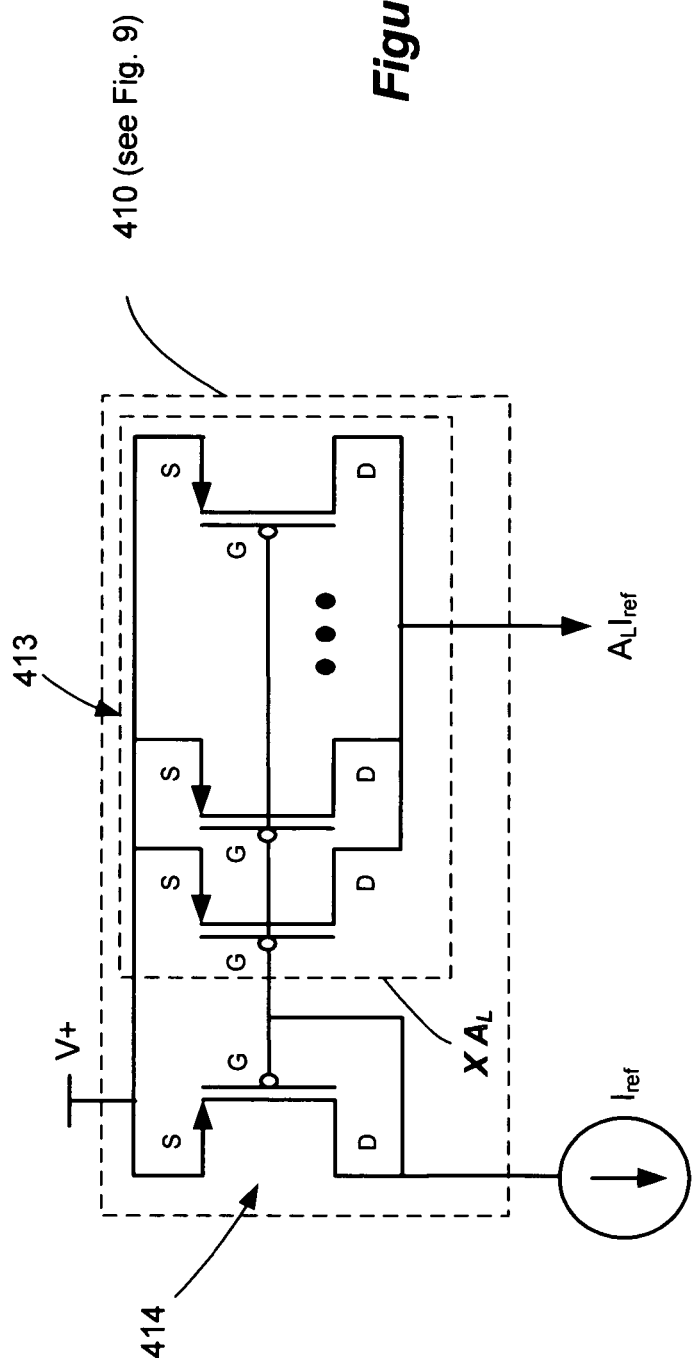
FIG. 10 shows the current mirror circuitry useable in the architecture of FIG. 9.
Figure 11:
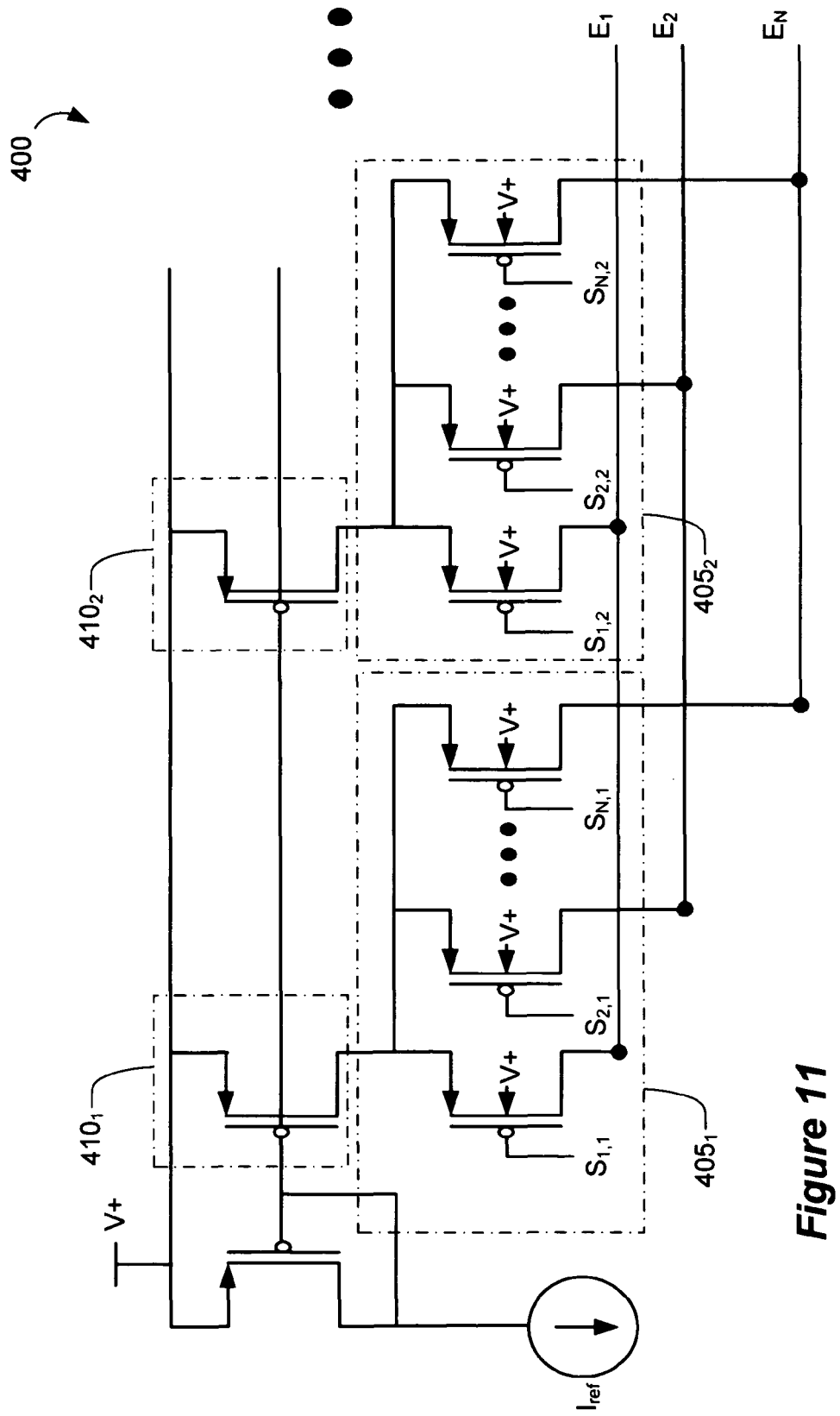
FIG. 11 shows a preferred current source/sink architecture in which a scalar of one is used in each stage.

New, improved output current architectures are illustrated in FIGS. 9-11. The new architectures, like previous architectures, employ output current source and output current sink circuitry, respectively labeled in FIG. 9 as circuitry 400 and 401, which would logically be implemented for example on analog IC 190' (FIG. 8). However, as is unique to the circuitry of FIGS. 9-11, and unlike the prior art architecture of FIGS. 2A and 3, each electrode $E_1$ through $E_N$ on the IPG 100 does not have its own dedicated, hard-wired source and sink circuitry. Instead, the source and sink circuitry 400, 401 is shared amongst the various electrodes $E_X$, via a network of switch banks, as will be explained below.

Figure 4:
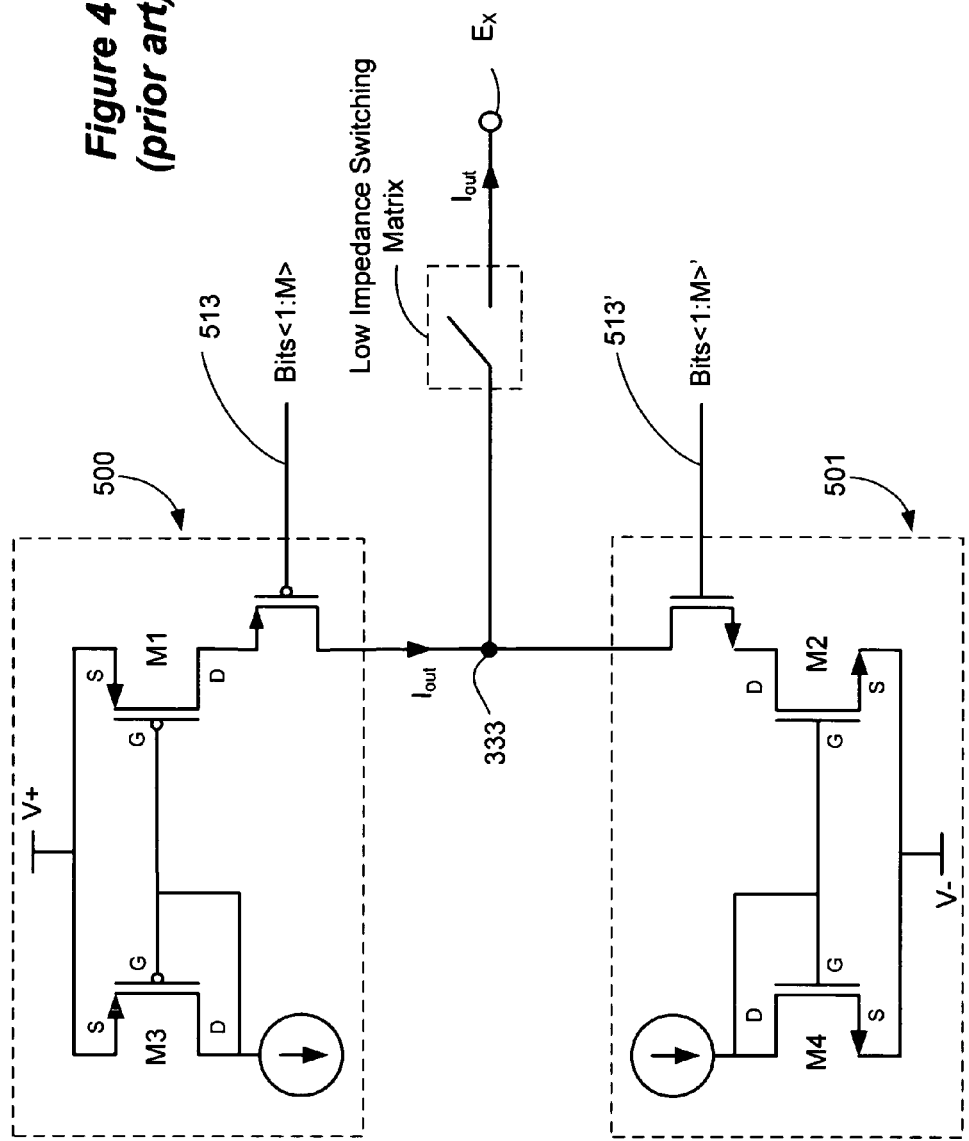
FIG. 4 shows drawbacks related to the architecture of FIG. 2B.

Moreover, and unlike the prior art architecture of FIGS. 2B and 4, and ignoring impedances such as coupling capacitances $C_N$ (FIG. 7) for reasons to be explained later, it is noticed that the PDACs and NDACs do not share a common node (such as node 333 in FIG. 2B) other than the electrode nodes. As a result, circuitry is not left intentionally unused as it was in the architecture of FIG. 2B, in which at least one of the PDAC and NDAC in a particular pair must remain unused at any particular point in time. Furthermore, as compared to the switch matrix approach of FIG. 2B and FIG. 4, the new architectures of FIGS. 9 and 11 comprise one less component in the output path, which reduces unwanted voltage drops in the output path, and results in power savings. As can be seen with brief reference to FIG. 11, which shows a PDAC current source 400, only two components intervene between the power supply V+ and a given electrode: the current mirror transistor(s) and the selection switch $S_{N,L}$ from the switch bank. In effect, and by comparison to FIG. 4, the bit select transistor and the switch in the low impedance switching matrix are combined into a single switch in the new architecture, saving both layout space and power. Moreover, further power savings are realized by the new architecture of FIGS. 9-11, but before this is understood these Figures are first discussed in more detail below.

The source circuitry 400 is primarily shown in FIG. 9, whereas the sink circuitry 401 is illustrated in mere dotted lines, which reflects this disclosure's focus on discussion of the output current source circuitry 400. However, the sink circuitry 401, while not specifically discussed, is similar in design and function to the source circuitry 400, although differing in polarity (e.g., connection to negative power supply V−, use of N-channel transistors, etc.).

As shown, the source circuitry 400 comprises a PDAC 407, various current mirrors 410, and various switch banks 405. Specifically, there are L number of current mirrors 410 and switch banks 405, and each switch bank comprises N switches, corresponding to the number of electrodes on the IPG 100. In other words, there are a total of N*L switches in the switch banks 405.

PDAC 407 converts an initial reference current $I_1$ to a true reference current $I_{ref}$ that is sent as an input to each of the current mirrors 410. The PDAC 407 can comprise any structure known in the art for allowing the amplification of current on the basis of digital inputs. For example, the PDAC can be constructed as in FIG. 3. However, any other design could be used, and in fact, use of PDAC 407 is not strictly required in all useful embodiments of the invention. However, it does have utility in setting the overall resolution and magnitude of the output currents to be supplied to the various electrodes $E_X$, as will be explained in further detail below.

The various current mirrors 410 take the reference current $I_{ref}$ and scale that current to produce currents of desired magnitudes in each of the L stages. Thus, the first stage scales $I_{ref}$ by $A_1$, the second by $A_2$, and so on. The various scalars $A_1$, $A_2, \ldots A_L$, can be different or can be the same in each of the stages. For example the scalars can exponentially increase ($A_1=1, A_2=2, A_3=4, A_4=8$, etc.), or linearly increase ($A_1=1, A_2=2, A_3=3$, etc.), or can stay the same. In fact, in a preferred embodiment, each of the scalars $A_L=1$, and thus each of the L stages merely takes the reference current $I_{ref}$ and outputs that current to their respective switch banks 405. (In this sense, a current can be said to be "scaled" even if the scalar at the stage equals one.) The scalars $A_L$ in each stage can be set by varying the number of transistors placed in parallel in the output stages of the current mirrors 410, as is shown in FIG. 10. Thus, were a ×4 gain desired, four P-channel transistors 413 would be placed in parallel with the balancing transistor 414 in the current mirror. Thus, in the preferred embodiment, only one transistor 413 would be used in each current mirror stage 410, such as is illustrated in FIG. 11. Although FIG. 11 shows the source 400, it would be understood that an N-channel transistors based sink 401 would be similarly constructed in a preferred embodiment.

Figure 1:
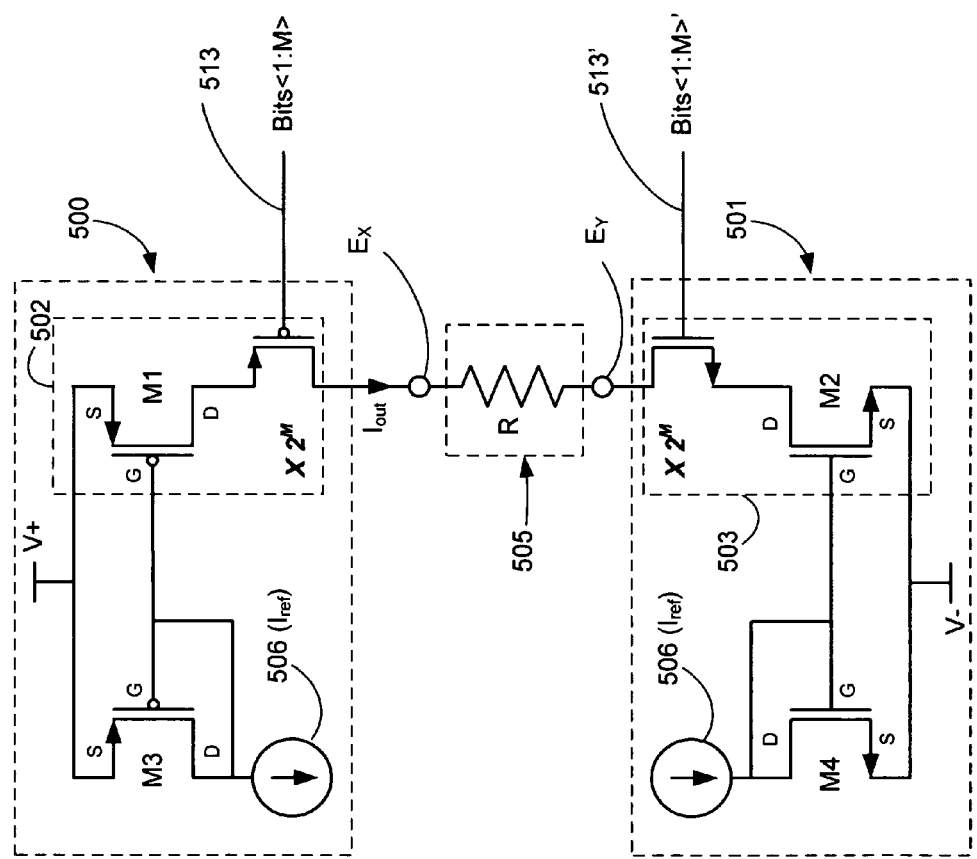
FIG. 1 shows an exemplary output current source and a corresponding output current sink each having current digital-to-analog converter (DAC) circuitry in series with a load.
Figure 2A:
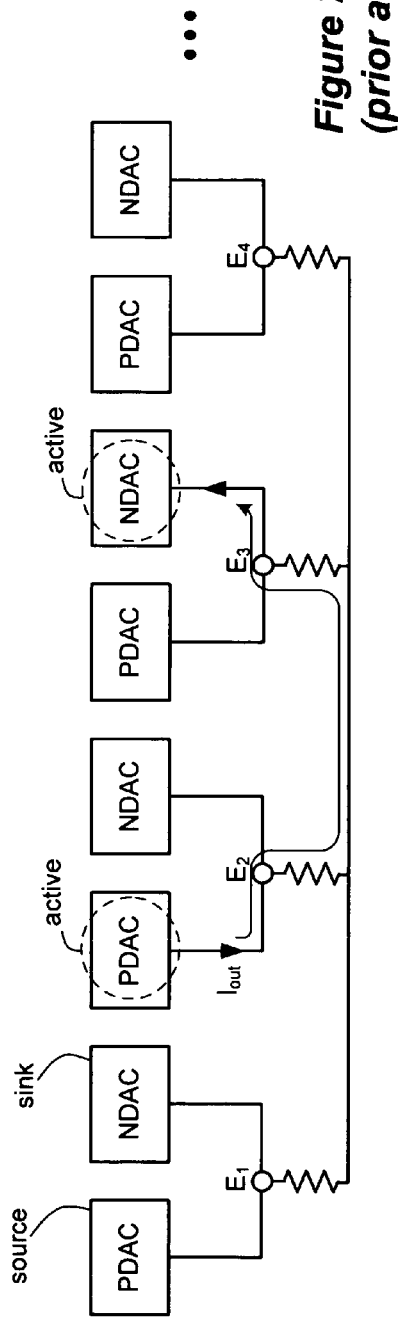
FIG. 2A shows a prior art architecture for coupling output current sources and sinks to a plurality of electrodes using hard-wired dedicated circuitry at each electrode.
Figure 2B:
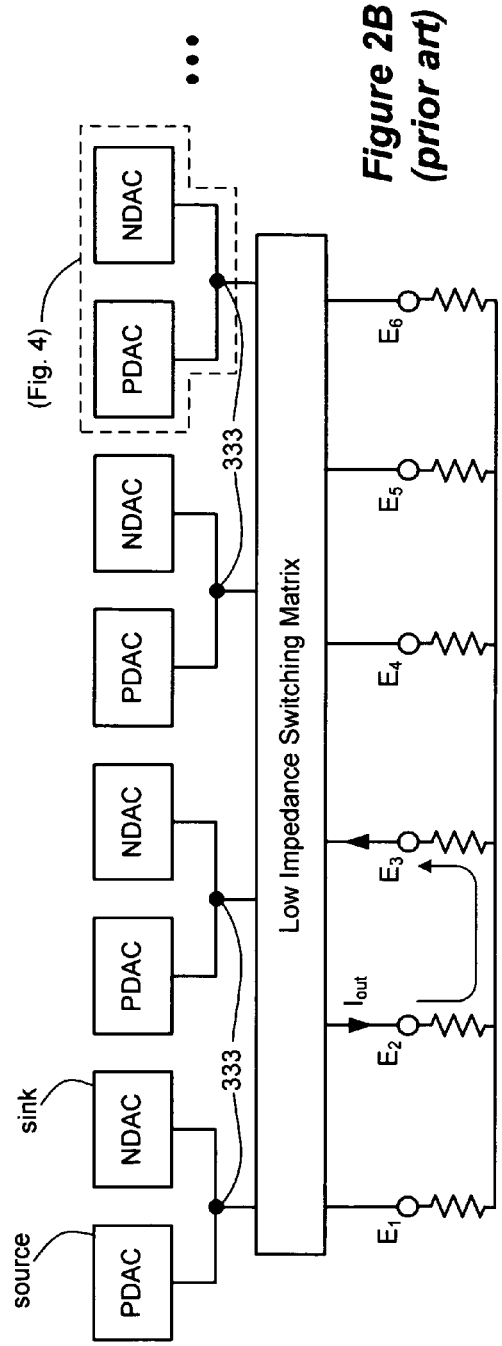
FIG. 2B shows a prior art architecture for coupling output current source and sinks to a plurality of electrodes using a switching matrix.
Figure 3:
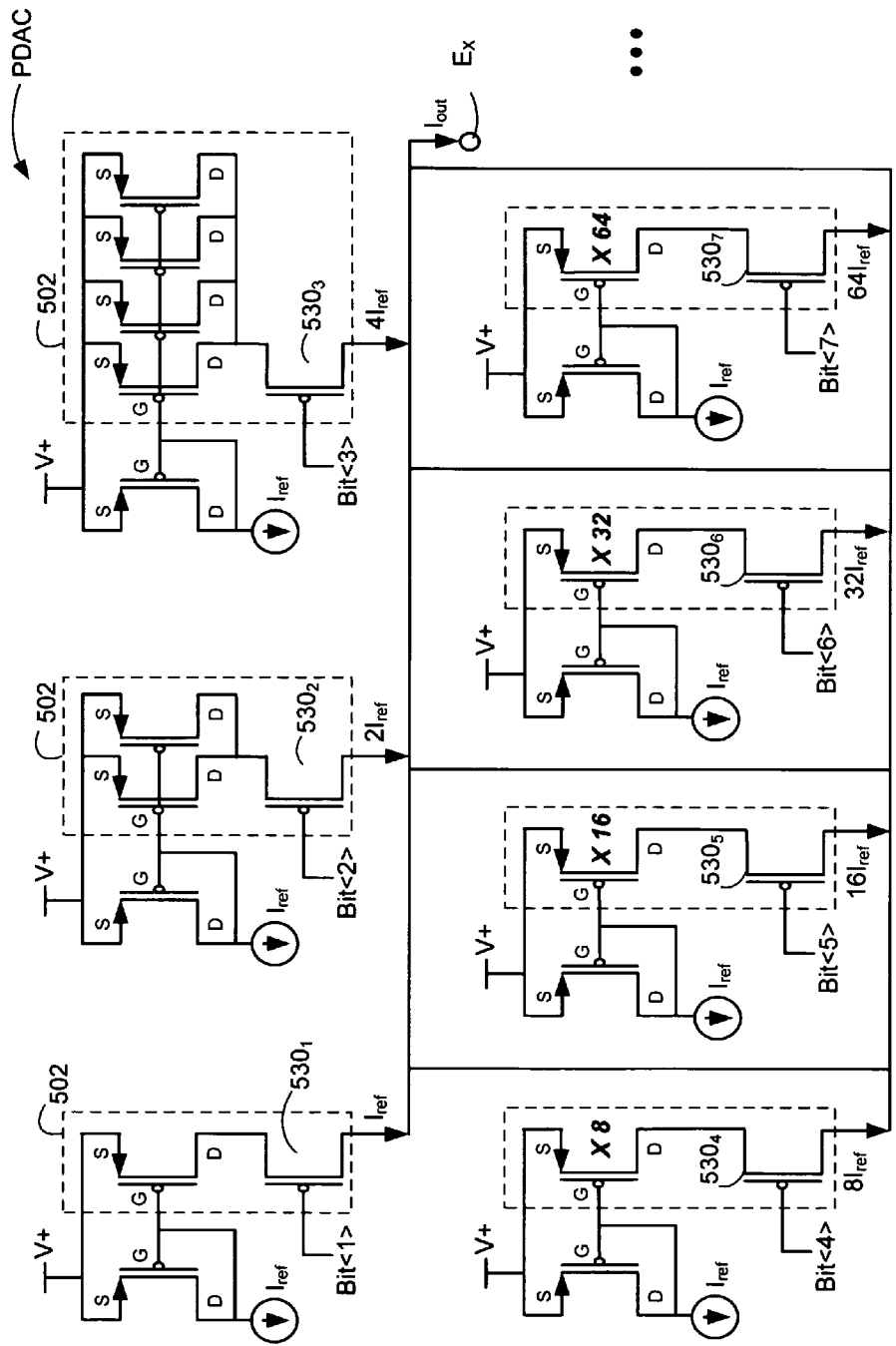
FIG. 3 shows the layout complexity of the output current sources of FIG. 2A.

In further distinction to the architecture of FIGS. 2A and 3, note that the current mirrors 410 are not individually selectable in and of themselves, i.e., they do not have bit select transistors as in the DAC of FIG. 3. They are always on and supplying current to the switch banks 405, with selection or not of a particular current mirror 410's current occurring in its given switch bank 405.

It should be noted that current mirrors 410 are simply one example of a current converter, i.e., a circuit used to convert one current ($I_{ref}$) to another current ($A_x I_{ref}$). Many other circuits capable of performing this function are known in the art, as thus the use of current mirrors in each stage should be understood as merely exemplary. Moreover, notice that unlike the various PDAC circuits of FIG. 2B, the current mirrors 410 of FIG. 9 are non-selectable, i.e., they always are enabled to provide their currents to the switch banks 405. In short, the disclosed architecture is simpler in that an additional layer of selection over and beyond selection of the various switches $S_X$ in the switch banks 405 is not necessary.

As noted earlier, the switch bank 405 for each stage receives the output of the current mirrors 410, i.e., $I_{ref}$ in the preferred embodiment. As shown in FIGS. 9 and 11, each switch bank 405 contains N switches, $S_N$, each of which is capable of routing the output current from its current mirror $410_x$ ($A_x I_{ref}$) to any of the electrodes $E_X$ on the IPG 100. Thus, in each stage, switch $S_1$ can send that stage's current to $E_1$, switch $S_2$ to $E_2$, etc. Accordingly, each stage is controllable to send its output current to more than one of the plurality of electrode nodes and thus can affect the current at any given electrode, and multiple stages can work together to produce a current at a given electrode. For example, assume each current mirror 410 has a scalar A of 1, such that each sends $I_{ref}$ to its respective switch bank 405. Assume further that there are 128 stages, such that all current mirrors 410 together can supply a maximum current of $128 I_{ref}$. Referring back to the example discussed in the Background, were a current of $53 I_{ref}$ desired at electrode $E_2$, switches $S_2$ could be closed in any 53 of the various stages (e.g., the first 53 stages, the last 53 stages, etc.). Similarly, multiple electrodes can be stimulated at the same time, i.e., to form one of the k channels discussed earlier. For example, suppose $53 I_{ref}$ is desired at electrode $E_2$; $12 I_{ref}$ at electrode $E_5$, and $19 I_{ref}$ at electrode $E_8$. This would require simultaneously closing 53 $S_2$ switches, 12 $S_5$ switches, and 19 $S_8$ switches.

At this point, certain aspects of the new architecture are worth noting. First, the minimum current that can be sent to any particular electrode $E_X$ is $I_{ref}$, which would comprise the selection of that electrode's switch in only one stage with a scalar of one. (This minimum resolution does not consider other schemes for generating fractions of $I_{ref}$, such as are disclosed in the above-incorporated '969 patent. Of course, such schemes could be used in conjunction with the embodiments of FIGS. 9 and 11, but are not shown). Second, the maximum current that can be provided to any electrode (or combination of electrodes in one of k channels) at any given time is $(A_1+A_2+\ldots+A_L)*I_{ref}$, or $128 I_{ref}$ in keeping with the example in which the scalars in each stage equal one.

Noting these limitations, various preferred aspects of the architecture can be better appreciated. The first is the preference to set the scalars $A_x$ of all stages to one. By doing this, it is assured that the lowest resolution of current $I_{ref}$ is available to a given electrode at a given time. For example, suppose $I_{ref}$ is desired at electrode $E_4$ while $3 I_{ref}$ is desired at electrode $E5$. Were the scalars in the various stages exponential for example ($A_1=1, A_2=2, A_3=4, A_4=8$, etc.), one of these desired currents could not be realized, as the first stage's scalar ($A_1=1$) would be needed for both at the same time. Thus, by choosing the smallest resolution for each stage ($A_x=1$), it can be assured that the multiple electrodes can be supplied with minimum increments of current, and thus can be finely controlled.

This same benefit of guaranteed minimum resolution can also be realized in other ways. For example, a set number of the stages (but less than all) could be set to a scalar of one, while other stages take on different scalar values. For example, realizing that it would be rare that more than four electrodes $E_N$ would be stimulated at one time, four stages could be set with a scalar of one (guaranteeing the minimum resolution at the four electrodes); four other stages could be set with a scalar of two; yet four other stages could be set with a scalar of four; and so on in increasing exponential fashion. In other words, the scalars $A_x$ at the various stages can take on different values depending on desired resolution and other design objectives.

Note that to the extent that scalars of greater than one are used in the stages, the number of stages (i.e., the number of current mirrors 410 and associated switch banks 405) will decrease, assuming the current capacity stays constant. For example, for a $128 I_{ref}$ current capacity, scalars of $A_x=1$ will require 128 stages. This is more space intensive, but will have improved resolution control. By contrast, scalars increasing exponentially ($A_1=1, A_2=2, A_3=4, A_4=8$, etc.) would require only seven stages (for a total of essentially the same value of $127 I_{ref}$). This is less space intensive, and simplifies the design, but also has drawbacks regarding minimum resolution control as noted above. In short, the minimum resolution versus the number of stages desired in the output current source 400 has trade offs that should be considered for any particular design. Thus, while the use of stages with minimum resolution scalars is preferred, it is not the only way to design an embodiment of the invention, and the invention should not be understood as so limited.

The second preferred aspect of the disclosed architecture worthy of note is the inclusion of PDAC 407. The PDAC 407 scales the initial reference current $I_1$ by a factor of Z to produce the true reference current $I_{ref}$ sent to the current mirrors 410 (i.e., $I_{ref}=Z*I_1$). In this way, the currents ultimately sent to the electrodes can be further (and globally) varied by adjusting the gain of the PDAC 407. If smaller current resolutions are required at the electrodes $E_X$, Z can be reduced through appropriate digital control of the PDAC. If higher total currents are required, Z can likewise be increased. Additionally, because PDAC 407 is digitally controllable, it can be controlled at one point in time to provide a low gain (low Z) or no gain (Z=1), while at other times providing a high gain (high Z). Thus, PDAC 407 provides greater control to the range of currents that can ultimately be provided at the electrodes $E_X$. This being said however, PDAC 407 is not required in all embodiments of the invention.

As noted earlier, in a preferred embodiment, the switch banks 405 would in total comprise N*L switches, where N equals in number of electrodes and L equals the number of stages in the output circuitry 400 (or 401). However, it should be noted that not every stage L would necessarily require N switches. For example, a given stage might comprise less than N switches, foregoing the ability to send that stage's current to a particular electrode $E_X$. Moreover, it is not necessary that every Xth switch in the switch banks 405 provide current to the Xth electrode, $E_X$. In short, while FIG. 9 illustrates a preferred embodiment, other designs within the scope of this disclosed embodiment are possible that still achieve the benefits of the architecture disclosed herein.

Control of the N switches in the various L stages can be easily accomplished through well-known addressing techniques. For example, control logic (like control logic 166 of FIG. 7) can output an address for the stages, and the various switches $S_X$ in that stage, that should be activated at a particular point in time to produce a desired current at a given electrode $E_x$. In this sense, the control signals to be sent to open or close the switches $S_X$ should be understood as loosely akin to the control signals on bus 513 in the prior art architecture of FIGS. 2A & 3. It should be understood that the switches $S_X$ are preferably single transistors of a logical polarity depending on whether they are present in the source circuitry 400 (P-channels) or the sink circuitry 401 (N-channels). However, other structures could also be used for the switches $S_X$, such as pass gates or transmission gates, etc.

It should be understood that the direction in which current flows is a relative concept, and different conventions can be used to define whether currents flow to or from various sources. In this regard, arrows showing the directions of current flows in the Figures, references to current flowing to or form various circuit nodes, references to currents being sunk or sourced, etc., should all be understood as relative and not in any limiting sense.

It should also be understood that reference to an electrode node implantable adjacent to tissue to be stimulated includes electrodes on the implantable stimulator device, or associated electrode leads, or any other structure for stimulating tissue.

Moreover, it should be understood that an "electrode node implantable adjacent to tissue to be stimulated" is to be understood without regard to any output capacitance, such as coupling capacitances $C_N$ included in the header connector 192 or elsewhere (see FIG. 7). It should be understood that nodes on both sides of such a coupling capacitor or other output impedance are, in the context of this invention, not materially different from an architectural standpoint, such that either node would be considered as the electrode node implantable adjacent to tissue to be stimulated. Thus, and referring to FIG. 7, even though a coupling capacitor $C_1$ has been used between the DAC circuitry 186 and the electrode node E1, both node $E_1$ and node 450 would be considered as "electrode nodes implantable adjacent to tissue to be stimulated" in the context of the present invention. Thus, node 450 would not comprise a common node between the source and sink circuitry different from the electrode node $E_1$, as node 450 is synonymous with node $E_1$ in the context of the invention. In short, the phrase "wherein the current source circuitry and the current sink circuitry do not share a common node other than the electrodes" should not be interpreted such that node 450 would be a common node other than the electrode nodes, because as just mentioned node 450 would be synonymous with the electrode node $E_1$. The same would be true for other impedances, e.g., if an output resistor was used in addition to or in lieu of coupling capacitor $C_1$.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. An implantable stimulator device, comprising:
    a plurality of electrode nodes for stimulating tissue;
    a plurality of current source stages, each current source stage comprising:
        a current source for sourcing a sourced output current, and
        a switch bank, wherein each switch bank comprises a plurality of switches each connected directly to one of the electrode nodes for receiving the sourced output current and for directing the sourced output current to any of the plurality of electrode nodes; and
    a plurality of current sink stages, each current sink stage comprising:
        a current sink for sinking a sinked output current, and
        a switch bank, wherein each switch bank comprises a plurality of switches each connected directly to one of the electrode nodes for receiving the sinked output current and for directing the sinked output current from any of the plurality of electrode nodes.

2. The implantable stimulator device of claim 1, wherein the current sources and current sinks comprise current converter circuits for converting a reference current into the sourced and sinked output currents representing a scaled version of the reference current.

3. The implantable stimulator device of claim 2, further comprising a digital-to-analog converter for converting another current into the reference current in accordance with digital control signals.

4. The implantable stimulator device of claim 2, wherein the current sources and the current sinks comprises current mirrors.

5. The implantable stimulator device of claim 4, wherein a scalar between the reference current and the output currents is set by a number of parallel output transistors in each current mirror.

6. The implantable stimulator device of claim 1, wherein the current sources and current sinks output pre-set sourced and sinked output currents.

7. The implantable stimulator device of claim 1, wherein the sourced output current is the same in each of the current source stages, and wherein the sinked output current is the same in each of the current sink stages.

8. The implantable stimulator device of claim 1, wherein the sourced output currents are linear across the current source stages, and wherein the sinked output currents are linear across the current sink stages.

9. The implantable stimulator device of claim 1, wherein the sourced output currents are exponential across the current source stages, and wherein the sinked output currents are exponential across the current sink stages.

10. The implantable stimulator device of claim 1, wherein there are L current sources stages and L current sink stages, wherein there are N switches in each of those stages, and wherein there are N electrodes.

11. The implantable stimulator device of claim 1, wherein the currents at each electrode comprise the sum of the sourced or sinked output currents provided by each of the stages.

12. An implantable stimulator device, comprising:
a plurality of electrode nodes for stimulating tissue;
a source generator for producing a source reference current;
a sink generator for producing a sink reference current;
a plurality of current source stages, each current source stage comprising:
a current source for converting the source reference current into an sourced output current representing a scaled version of the source reference current, and
a switch bank, wherein each switch bank comprises a plurality of switches each connected directly to one of the electrode nodes for receiving the sourced output current and for directing the sourced output current to any of the plurality of electrode nodes; and
a plurality of current sink stages, each current sink stage comprising:
a current sink for converting the sink reference current into a sinked output current representing a scaled version of the sink reference current, and
a switch bank, wherein each switch bank comprises a plurality of switches each connected directly to one of the electrode nodes for receiving the sinked output current and for directing the sinked output current from any of the plurality of electrode nodes.

13. The implantable stimulator device of claim 12, wherein the source and sink generators comprise digital-to-analog converters.

14. The implantable stimulator device of claim 12, wherein the current sources and the current sinks comprises current mirrors.

15. The implantable stimulator device of claim 14, wherein a scalar between the reference current and the output currents is set by a number of parallel output transistors in each current mirror.

16. The implantable stimulator device of claim 12, wherein the current sources and current sinks output pre-set sourced and sinked output currents.

17. The implantable stimulator device of claim 12, wherein the sourced output current is the same in each of the current source stages, and wherein the sinked output current is the same in each of the current sink stages.

18. The implantable stimulator device of claim 12, wherein the sourced output currents are not the same in each of the current source stages, and wherein the sinked output currents are not the same in the current sink stages.

19. The implantable stimulator device of claim 12, wherein there are L current sources stages and L current sink stages, wherein there are N switches in each of those stages, and wherein there are N electrodes.

20. The implantable stimulator device of claim 12, wherein the currents at each electrode comprise the sum of the sourced or sinked output currents provided by each of the stages.

21. An implantable stimulator device, comprising:
a plurality of N electrode nodes for stimulating tissue;
a plurality of L current source stages, each current source stage comprising:
a current source for sourcing a sourced output current, and
a switch bank, wherein each switch bank comprises a plurality of switches each connected directly to one of the electrode nodes for receiving the sourced output current and for directing the sourced output current to any of the plurality of electrode nodes; and
a plurality of L current sink stages, each current sink stage comprising:
a current sink for sinking a sinked output current, and
a switch bank, wherein each switch bank comprises a plurality of switches each connected directly to one of the electrode nodes for receiving the sinked output current and for directing the sinked output current from any of the plurality of electrode nodes.

22. The implantable stimulator device of claim 21, wherein the current sources and current sinks comprise current converter circuits for converting a reference current into the sourced and sinked output currents representing a scaled version of the reference current.

23. The implantable stimulator device of claim 22, further comprising a digital-to-analog converter for converting another current into the reference current in accordance with digital control signals.

24. The implantable stimulator device of claim 22, wherein the current sources and the current sinks comprises current mirrors.

25. The implantable stimulator device of claim 24, wherein a scalar between the reference current and the output currents is set by a number of parallel output transistors in each current mirror.

26. The implantable stimulator device of claim 21, wherein the current sources and current sinks output pre-set sourced and sinked output currents.

27. The implantable stimulator device of claim 21, wherein the sourced output current is the same in each of the current source stages, and wherein the sinked output current is the same in each of the current sink stages.

28. The implantable stimulator device of claim 21, wherein the sourced output currents are not the same in each of the current source stages, and wherein the sinked output currents are not the same in the current sink stages.

29. The implantable stimulator device of claim 21, wherein N does not equal L.

* * * * *

UNITED STATES PATENT AND TRADEMARK OFFICE
CERTIFICATE OF CORRECTION

PATENT NO.       : 8,606,362 B2                                                          Page 1 of 1
APPLICATION NO. : 11/177503
DATED            : December 10, 2013
INVENTOR(S)      : He et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 980 days.

Signed and Sealed this
Twenty-third Day of May, 2017

Michelle K. Lee
*Director of the United States Patent and Trademark Office*

UNITED STATES PATENT AND TRADEMARK OFFICE

(12)          CERTIFICATE EXTENDING PATENT TERM
UNDER 35 U.S.C. § 156

| | | |
|---|---|---|
| (68) | PATENT NO. | :    8,606,362 |
| (45) | ISSUED | :    December 10, 2013 |
| (75) | INVENTOR | :    He et al. |
| (73) | PATENT OWNER | :    BOSTON SCIENTIFIC NEUROMODULATION CORPORATION |
| (95) | PRODUCT | :    VERCISE® Genus Deep Brain Stimulation System |

This is to certify that an application under 35 U.S.C. § 156 has been filed in the United States Patent and Trademark Office, requesting extension of the term of U.S. Patent No. 8,606,362 based upon the regulatory review of the product VERCISE® Genus Deep Brain Stimulation System by the Food and Drug Administration. According to United States Patent and Trademark Office records, the original expiration date of the patent as of the date of issuance of this certificate is March 14, 2028. Because it appears that the requirements of the law have been met, this certificate extends the term of the patent for the period of

(94)                                274 days subject to the payment of maintenance fees as provided by law, with all rights pertaining thereto as provided by 35 U.S.C. § 156.

I have caused the seal of the United States Patent and Trademark Office to be affixed this 17th day of November 2025.

John A. Squires
Under Secretary of Commerce for Intellectual Property and
Director of the United States Patent and Trademark Office